United States Patent
Kosaka et al.

(10) Patent No.: US 8,367,745 B2
(45) Date of Patent: Feb. 5, 2013

(54) DENTAL COMPOSITE RESIN FOR CORE BUILD-UP

(75) Inventors: Yugo Kosaka, Itabashi-ku (JP); Yutaka Shinozaki, Itabashi-ku (JP); Tomohiro Kumagai, Itabashi-ku (JP)

(73) Assignee: GC Corporation, Tokyo (JP)

( * ) Notice: Subject to any disclaimer, the term of this patent is extended or adjusted under 35 U.S.C. 154(b) by 149 days.

(21) Appl. No.: 12/058,090

(22) Filed: Mar. 28, 2008

(65) Prior Publication Data

US 2008/0242756 A1    Oct. 2, 2008

(30) Foreign Application Priority Data

Mar. 30, 2007 (JP) ................................. 2007-090767

(51) Int. Cl.
- C08F 20/18 (2006.01)
- C08F 2/50 (2006.01)
- C08F 4/40 (2006.01)
- C08F 4/34 (2006.01)
- C08F 4/50 (2006.01)
- A61K 6/08 (2006.01)
- A61K 6/083 (2006.01)
- A61C 5/04 (2006.01)

(52) U.S. Cl. ............ 522/182; 522/10; 522/60; 523/113; 523/115; 523/116; 433/226; 433/228.1; 106/35; 526/123.1; 526/217; 526/227

(58) Field of Classification Search .............. 443/224; 522/83, 182, 10, 60; 523/116, 115, 118, 523/113; 433/228.1, 226; 106/35; 526/123.1, 526/217, 227

See application file for complete search history.

(56) References Cited

U.S. PATENT DOCUMENTS

| | | | |
|---|---|---|---|
| 4,567,030 A * | 1/1986 | Yuasa et al. ................... | 423/326 |
| 5,609,675 A * | 3/1997 | Noritake et al. ................ | 106/35 |
| 5,688,492 A * | 11/1997 | Galley et al. .................... | 424/49 |
| 6,500,004 B2 * | 12/2002 | Jensen et al. ............... | 433/228.1 |
| 6,572,693 B1 | 6/2003 | Wu et al. | |
| 2004/0235981 A1 * | 11/2004 | Qian ............................ | 523/115 |
| 2005/0252413 A1 | 11/2005 | Kangas et al. | |
| 2006/0047012 A1 * | 3/2006 | Wagner et al. ................ | 523/115 |
| 2007/0039519 A1 * | 2/2007 | Kangas et al. .................. | 106/35 |

FOREIGN PATENT DOCUMENTS

| | | |
|---|---|---|
| JP | 9-157126 | 6/1997 |
| WO | WO 98/46197 | 10/1998 |

* cited by examiner

*Primary Examiner* — Michael Pepitone
(74) *Attorney, Agent, or Firm* — Oblon, Spivak, McClelland, Maier & Neustadt, L.L.P.

(57) ABSTRACT

To provide a dual curing type composite resin for core build-up having improved curing property by chemical polymerization with improved mechanical strength of a cured body under the condition of no light irradiation and with a shortened setting time, the composite resin is composed of a first component including a (meth)acrylate polymerizable resin and an organic peroxide, and a second component including (meth)acrylate polymerizable resin and a reducing agent, a photopolymerizaton initiator and a filler are included in the first component and/or the second component, and oxide powder of a Group II element in the periodic table having an average particle diameter of 1 μm or less is blended in the first component and/or the second component.

12 Claims, No Drawings

DENTAL COMPOSITE RESIN FOR CORE BUILD-UP

BACKGROUND OF THE INVENTION

1. Field of the Invention

The present invention relates to a dual curing type composite resin for core build-up.

2. Description of the Conventional Art

In a case of fixing a dental prosthesis at a residual tooth, when the residual tooth is in an almost healthy state, this residual tooth is cut by a turbine so as to have an approximately truncated conical shape, and is used as an abutment tooth. However, when a residual tooth is remarkably damaged and only remains as a dental root portion, an operation to reinforce holding force of the abutment tooth is carried out by inserting a post into a root canal, implanting it, and core build-up model with a substance which substitutes a dentin. Thereafter, the abutment tooth is cut by a turbine so as to have an approximately truncated conical shape for use as a abutment tooth.

When such an abutment tooth model is built, a specific composite resin for core build-up has been generally used. This composite resin has high penetrability into a narrow part of a root canal and thus an abutment tooth can easily be built. Such the composite resin for core build-up (it may be called as only a composition hereinafter) is a photopolymerizable material, so that an operator can adjust viscosity of the composition by irradiating light for a proper time whenever the operator wants. Further, when an operator wants to complete polymerizing of the composition, the composition can be rapidly cured by fully irradiating light, and thus handling of the composition can be easily controlled.

On the other hand, when a post is implanted, a dual curing type composition, which is cured by photopolymerization and chemical polymerization, has been used (for example, refer to Unexamined Japanese Patent Publication No. H9-157126) in order to sufficiently cure a composition flowed into the inside of a root canal and a cavity bottom part where light hardly reaches. However, as for the conventional dual curing type composition, since polymerizing at the portion where light hardly reaches depends on only a chemical polymerization, an effect by a photopolymerization cannot be expected, and mechanical strength of a cured body may be lower than a designed value. Further, a time until the composition becomes capable of being cut by using a turbine to have a shape of an abutment tooth depends on a speed of a chemical polymerization of the composition flowed into a root canal. Thus, it is desirable for both an operator and a patient that the speed of the chemical polymerization increases within the range not to affect preservation property of a composition.

SUMMARY OF THE INVENTION

An objective of the present invention is to provide such a dual curing type composite resin for core build-up that curing property by chemical polymerization is improved so that mechanical strength of a cured body at the inside of a root canal and a cavity bottom part, where light hardly reaches, can be improved and a setting time can be shorten.

Present inventors carried out earnest works to realize the above-described objective, and they found out the followings to complete the present invention. The objective can be realized by mixing oxide powder of a Group II element in the periodic table having an average particle diameter of 1 μm or less in a conventional dual curing type composite resin for core build-up, and promoting a redox reaction by using an organic peroxide and a reducing agent.

That is, according to the present invention, a composite resin for core build-up is composed of a first component including a (meth)acrylate polymerizable resin and an organic peroxide and a second component including (meth)acrylate polymerizable resin and a reducing agent, a photopolymerizaton initiator and a filler are included in the first component and/or the second component, and oxide powder of a Group II element in the periodic table having an average particle diameter of 1 μm or less is blended in the first component and/or the second component.

The composite resin for core build-up according to the present invention is such a dual curing type composite resin for core build-up that mechanical strength of a cured body under the condition of not irradiating light is improved in comparison with that of a conventional chemical polymerization type composition, and a setting time for clinical treatment is shorten.

DETAILED DESCRIPTION OF PREFERRED EMBODIMENT

As a (meth)acrylate polymerizable resin used in the present invention, a (meth)acrylate polymerizable resin conventionally used in a dental field can be used, and kinds, numbers, and molecular weights of a polymerizable group can be properly selected.

The (meth)acrylate polymerizable resin is, for example, methyl(meth)acrylate, ethyl(meth)acrylate, isopropyl(meth)acrylate, 2-hydroxyethyl(meth)acrylate, 2-hydroxypropyl (meth)acrylate, 2-hydroxy-1,3-di(meth)acryloxypropane, n-butyl(meth)acrylate, isobutyl(meth)acrylate, butoxyethyl (meth)acrylate, hydroxypropyl(meth)acrylate, tetrahydrofurfuryl(meth)acrylate, glycidil(meth)acrylate, 2-methoxyethyl (meth)acrylate, 2-ethylhexyl(meth)acrylate, benzyl(meth)acrylate, ethyleneglycol di(meth)acrylate, diethyleneglycol di(meth)acrylate, triethyleneglycol di(meth)acrylate, triethyleneglycol tri(meth)acrylate, butyleneglycol di(meth)acrylate, neopentylglycol di(meth)acrylate, 1,3-butanediol di(meth)acrylate, 1,4-butanediol di(meth)acrylate, 1,6-hexanediol di(meth)acrylate, trimethylolpropane tri(meth)acrylate, trimethylolethane tri(meth)acrylate, trimethylolethane tri(meth)acrylate, pentaerythritol tri(meth)acrylate, pentaerythritol tetra(meth)acrylate, polyoxytetraethyleneglycol di(meth)acrylate, 2,2-bis{(meth)acryloxyphenyl}propane, 2,2-bis[4-{2-hydroxy-3-(meth)acryloxypropoxy}phenyl]propane, 2,2-bis{4-(meth)acryloxydiethoxyphenyl}propane, 2,2-bis{4-(meth)acryloxypolyethoxyphenyl}propane, 2,2-bis[4(2-hydroxy-3-methacryloxypropoxy)phenyl]propane, or di-2-(meth)acryloxyethyl-2,2,4-trimethylhexamethylene dicarbamate as (meth)acrylate having an urethane bond in a molecule. These methacrylates and acrylates can be mixed to be used. Further, in addition to those, of course, an oligomer, a (meth)acrylate polymerizable resin having a phosphoric acid group, or a (meth)acrylate polymerizable resin having a carboxylic acid group can be used.

The blending amount of a (meth)acrylate polymerizable resin is preferably 10 to 60% by weight in each of the first component and the second component. When the amount is less than 10% by weight, the blending amount of a polymerization catalyst as the other component decreases relatively, and thus curing property of a composition may decrease. When the amount is more than 60% by weight, strength as a composite resin for core build-up may be insufficient.

In the present invention, a conventional organic peroxide, reducing agent, photopolymerization initiator and filler can be used. The organic peroxide is preferably diacyl peroxides having an aromatic group or peroxide esters regarded as ester of perbenzoic acid. For example, the organic peroxide is benzoyl peroxide, 2,4-dichlorobenzoyl peroxide, m-toluene peroxide, t-butylperoxy benzoate, di-t-butylperoxyisophthalate, or 2,5-dimethyl-2,5 di(benzoylperoxy) hexane is effective. This organic peroxide is necessarily used as a different component from a reducing agent mentioned below.

An amine compound for the reducing agent is effectively aromatic tertiary amines or aliphatic tertiary amines. More particularly, the amine compound is N,N-dimethyl-p-toluidine, N,N-diethyl-p-toluidine, N,N-dimethylaniline, N,N-bis (2-hydroxyethyl)-p-toluidine, N,N-dimethylaminoethyl-methacrylate, p-toluenediethanol amine, triethanol amine, p-dimethylamino methyl benzoate, p-dimethylamino ethyl benzoate, p-dimethylamino isoamyl benzoate, triethyl amine, or N-ethyldiethanol amine. The amine compound can be used independently or by mixing two or more kinds.

A combination of peroxide and an amine compound has been generally used as a polymerization initiator. However, when an organic aromatic compound including at least one —$SO_2$— group is further added, polymerizability of a (meth)acrylate polymerizable resin under acidity can be improved. The organic aromatic compound including at least one —$SO_2$— group is aromatic group sulfinic acid or its metal salt, or an aromatic group sulfonyl compound. For example, the organic aromatic compound including at least one —$SO_2$— group is sodium p-toluenesulfinate, lithium p-toluenesulfinate, benzene sulfinic acid, sodium benzenesulfinate, p-toluenesulfonyl chloride, p-toluenesulfonyl fluoride, o-toluenesulfonyl isocyanate, p-toluenesulfonyl hydrazide, p-toluenesulfonamide, p-toluenesulfonyl imidazole, p-toluenesulfonyl cyanide, 2-(p-toluenesulfonyl)acetophenone, p-toluenesulfonyl-N-diethylamide, α-N,α-toluenesulfonyl-N-arginine, αN,p-toluenesulfonyl-L-argininemethyl ester, p-toluenesulfonyl methylisocyanate, p-toluenesulfonyl-N-methyl-N-nitrosamide, N-(p-toluenesulfonyl)-L-phenylalanine, N-p-toluenesulfonyl-L-phenylalanyl chloride, p-toluenesulfonyl acetonitrile, 2-(p-toluenesulfonyl)acetophenone, toluene-3,4-disulfonyl chloride, benzene sulfonamide, benzene sulufohydroxyamine acid, benzenesulfonyl chloride, benzenesulfonyl isocyanate, benzene sulfone anilide, benzene sulfone chloramide sodium, benzene sulfone dichloramide, benzenesulfonyl hydrazide, benzenesulfonyl-N-methylamide, 2-phenylsulfonyl acetophenone, diamino diphenyl sulfone, 4,4'-sulfonyl diphenol, sulfapyridine, sulfaaerosol, sulfamethizole, ethylbenzenesulfonyl chloride, nitrobenzenesulfonyl chloride, or nitrobenzenesulfonyl fluoride. In addition, an organic aromatic compound including at least one —$SO_2$— group can be a salt hydrate.

The photopolymerization initiator is, for example, camphorquinone, benzyl, diacetyl, benzyl dimethyl ketal, benzyl diethyl ketal, benzyl di(2-methoxyethyl)ketal, 4,4'-dimethyl-benzyl-dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethylthioxanthone, thioxanthone-10,10-dioxide, thioxanthone-10-oxide, benzoinmethylether, benzomethylether, isopropylether, benzoinisobutylether, benzophenone, bis(4-dimethylaminophenyl) ketone, 4,4'-bisdiethylaminobenzophenone, a derivative of an acylphosphine oxide, or a compound including an azide group. These can be used independently or by mixing two or more kinds. In the present invention, a photopolymerization initiator can be blended in the first component or the second component.

Each blending amount of the organic peroxide, the reducing agent and the photopolymerization initiator is preferably 0.01 to 5 weight parts with respect to the total amount of 100 weight parts of a (meth)acrylate polymerizable resin in the component in which it is blended. When the amount is less than 0.01 weight parts, ability as a polymerization catalyst may be insufficient. When the amount is more than 5 weight parts, preservation stability of a component decreases.

The filler is, for example, glasses such as α-quartz, silica, silicic acid anhydride, a barium glass, an alumina glass, a potassium glass, hydroxyapatite, or a fluoroaluminosilicate glass, a barium borosilicate glass, barium boro-alumina silicate glass, powders such as synthetic zeolite, barium sulfate, titanium oxide, calcium phosphate, a feldspar, fumed silica, aluminum silicate, calcium silicate, magnesium carbonate, hydrous silicic acid, calcium silicate hydrate, or aluminum silicate hydrate, or an organic composite filler including an organic component and an inorganic component.

The filler can be subjected to a surface treatment with methyltrimethoxysilane, methyltriethoxysilane, methyltrichlorosilane, dimethyldichlorosilane, trimethylchlorosilane, vinyltrimethoxysilane, vinyltriethoxysilane, vinyltrichlorosilane, vinyltriacetoxysilane, vinyltris(2-methoxyethoxy)silane, 3-methacryloyloxypropyltrimethoxysilane, 3-methacryloyloxypropyltris(2-methoxyethoxy)silane, 3-methacryloxypropyltrimethoxysilane, 3-chloropropyltrimethoxysilane, 3-chloropropylmethyldimethoxysilane, 3-glycidiloxypropyltrimethoxysilane, 3-glycidiloxypropylmethyldiethoxysilane, 2-(3,4-epoxycyclohexyl)ethyltrimethoxysilane, 5,6-epoxyhexyltriethoxysilane, 3-ethyl-3-[3-(triethoxysilyl)propoxymethyl]oxetane, N-phenyl-γ-aminopropyltrimethoxysilane, or hexamethyldisilazane. Further, an organic and inorganic composite filler produced by mixing the filler with a (meth)acrylate polymerizable resin in advance, curing the mixture, and pulverizing it, can be also used. These filler can be used independently or by mixing two or more kinds. In the present invention, the filler can be blended in the first component or the second component.

Further, as a filler, a polymer of a (meth)acrylate polymerizable resin can be blended. More particularly, this polymer is, for example, a homopolymer of the (meth)acrylate polymerizable resin, a copolymer of two or more of the (meth)acrylate polymerizable resin, or a copolymer of various kinds of (meth)acrylate polymerizable resins and styrene. These polymers can be used independently or by mixing two or more.

The blending amount of the filler is preferably 40 to 90% by weight in the component in which it is blended. When the amount is less than 40% by weight, strength as a composite resin for core build-up may be insufficient. When the amount is more than 90% by weight, the flowability of the composition becomes too low at the time of using the composition, and thus the composition hardly flows into a narrow part of a root canal.

Oxide powder of a Group II element in the periodic table having an average particle diameter of 1 μm or less, which is blended in the first component and/or the second component, has an effect to control (neutralize) an influence from a silanol group, which works as acidity on the filler surface, so as to promote polymerizing, in redox chemical polymerization by an organic peroxide such as benzoyl peroxide and a reducing agent such as amine. The oxide powder of a Group II element in the periodic table is oxide powder of beryllium, magnesium, calcium, strontium or barium.

The particle diameter of the oxide powder of a Group II element in the periodic table used in the present invention is important, and the average particle diameter is necessarily 1 μm or less, and preferably from 0.01 to 0.2 μm. Oxide of a Group II element in the periodic table has no light transmittability. Thus, when the average particle diameter is more than 1 μm, light curing depth is decreased, so that it is not preferable. Oxide powder of a Group II element in the periodic table is classified as a part of the filler, but it is preferable that the surface of the powder is not subjected to a silane treatment.

The blending amount of the oxide powder of a Group II element in the periodic table is preferably 0.01 to 5% by weight in the first component and/or the second component. When the amount is less than 0.01% by weight, mechanical strength of a cured body may be insufficiently improved. When the amount is more than 5% by weight, mechanical strength of the cured body decreases, and further, light curing depth is decreased.

The composite resin for core build-up according to the present invention can be added with a polymerization inhibitor, an antioxidant, an antitarnish, an ultraviolet absorber, a surfactant, a pigment, a fragcance, and an antibacterial agent, which have been generally used in a dental resin material, within the range not to damage the properties.

EXAMPLES

The dental composite resin for core build-up according to the present invention will be described below with referent to Examples, but the present invention is not limited to these examples.

Examples 1 to 6, Comparative Examples 1 and 2

A first component and a second component were prepared at the blending ratios shown in Table 1. The first and second components were prepared by mixing a (meth)acrylate polymerizable resin with a reducing agent, an organic peroxide, and a photopolymerization initiator, then taking a filler into a mortar, and sufficiently kneading it so as to make a uniform paste. Materials used in Examples and Comparative examples are as follows.
<(Meth)Acrylate Polymerizable Resin>
Bis-GMA: 2,2-bis[4-(2-hydroxy-3-methacryloxypropoxy) phenyl]propane
UDMA: Di-2-(meth)acryloxyethyl-2,2,4-trimethylhexamethylene dicarbamate
TEGDMA: Triethyleneglycol dimethacrylate
HDMP: 2-hydroxy-1,3-dimethacryloxypropane
NPGDMA: Neopentylglycol dimethacrylate
<Filler>
[Filler Other than Oxide Powder of a Group II Element in the Periodic Table]
b1: Powder in which 100 weight parts of a fluoroaluminosilicate glass powder (having an average particle diameter of 3 μm) is subjected to a surface treatment with 3 weight parts of 3-methacryloyloxypropyltrimethoxysilane.
b2: Powder in which 100 weight parts of a fluoroaluminosilicate glass powder (having an average particle diameter of 8 μm) is subjected to a surface treatment with 1 weight part of 3-methacryloyloxypropyltrimethoxysilane.
b3: Fine silica powder (having an average particle diameter of 0.005 to 0.05 μm)

[Oxide Powder of a Group II Element in the Periodic Table]
c1: Magnesium oxide having an average particle diameter of 0.05 μm
c2: Magnesium oxide having an average particle diameter of 0.1 μm
c3: Magnesium oxide having an average particle diameter of 1.27 μm In Examples 1 to 6 and Comparative examples 1 and 2, the first component was blended with 1 weight part of benzoyl peroxide (BPO) as a polymerization catalyst and 0.2 weight parts of 2,6-di-tert-butyl-p-cresol (BHT) as a polymerization inhibitor with respect to 100 weight parts of a (meth)acrylate polymerizable resin. The second component is blended with 0.3 weight parts of camphorquinone (CQ) as a polymerization catalyst, 2.0 weight parts of p-toluenediethanol amine (p-amine) and 2.0 weight parts of p-dimethylamino ethyl benzoate (EPA) as reducing agents, and 0.2 weight parts of 2,6-di-tert-butyl-p-cresol (BHT) as a polymerization inhibitor with respect to 100 weight parts of a (meth)acrylate polymerizable resin.

<Three-Point Flexural Strength Test>

A test piece was produced by kneading an equivalent amounts of the first component and the second component, filling the mixture into a mold having a square hole having the size of 2×2×25 mm, pressing an upper part of the mixture with a propylene film while caring not to make bubbles therein, and chemically polymerizing the components. The test piece was mounted on a universal testing machine (the product name was Auto Graph AG-IS, produced by Shimadzu Corporation), and three-point flexural strength was measured at a span of 20 mm and a crosshead speed of 1.0 mm/min. The results were shown in Table 1.

<Measuring of a Setting Time>

The equivalent amounts of the first component and the second component were kneaded, and filled into a plastic tube for measuring a setting time. Then, a heat generating value of the kneaded paste was measured by using a thermocouple. When the heat generating showed the maximum value, the lapsed time from the start of kneading was defined to be a setting time and measured it. In addition, the measuring was carried out in a darkroom at constant temperature of 23° C. The results were shown in Table 1.

<Measuring of Light Curing Depth>

The equivalent amounts of the first component and the second component were kneaded, filled into a mold (having an inner diameter of 4 mm and a height of 8 mm) while caring not to make bubbles therein, and pressed with a glass plate through a transparent film. Then, one side was subjected to light irradiation for 20 seconds by a dental visible beam radiator (the product name was GC New Light VLII, produced by GC Corporation) so as to make a cured body, and then the cured body was rapidly taken out from the mold. An un-polymerized part of the cured body was removed by a gauze soaked with alcohol. Then, a residual cured body length was measured by a micrometer and an obtained value was defined to be a light curing depth. The results were shown in Table 1.

<Table 1>

Comparative example 1 was an example of the case that oxide powder of a Group II element in the periodic table were not blended. In this case, the flexural strength was lower than those of Examples, and a setting time was clearly longer than those of Examples.

Comparative example 2 was an example of the case that an average particle diameter of oxide powder of a Group II element in the periodic table was 1.27 μm. In this case, a setting time was slightly longer than those of Examples, and light curing depth was also worse than that of Examples.

TABLE 1

| Components | | Example 1 First | Example 1 Second | Example 2 First | Example 2 Second | Example 3 First | Example 3 Second | Example 4 First | Example 4 Second |
|---|---|---|---|---|---|---|---|---|---|
| (Meth)acrylate polymerizable resin | | 30 | 30 | 30 | 30 | 30 | 30 | 30 | 30 |
| Mixing Ratio | Bis-GMA | | | | | 18 | 18 | | |
| | UDMA | 24 | 24 | 24 | 24 | | | 21 | 21 |
| | TEGDMA | | 6 | | 6 | 12 | | | 9 |
| | HDMP | | | 6 | | | | | |
| | NPGDMA | 6 | | | | | 12 | 9 | |
| Filler | | 70 | 70 | 70 | 70 | 70 | 70 | 70 | 70 |
| Mixing Ratio | b1 | 25 | 25 | 25 | 25 | 30 | 30 | 35 | 35 |
| | b2 | 69 | 69 | 67 | 66 | 65 | 64 | 60 | 59 |
| | b3 | 5 | 5 | 8 | 8 | 5 | 5 | 5 | 5 |
| | c1 | 1 | 1 | | 1 | | 1 | | 1 |
| | c2 | | | | | | | | |
| | c3 | | | | | | | | |
| Flexural Strength (Mpa) | | 130 | | 132 | | 135 | | 128 | |
| Setting Time | | 7 minutes and 45 seconds | | 7 minutes and 30 seconds | | 8 minutes and 15 seconds | | 8 minutes | |
| Light Curing Depth (mm) | | 4.7 | | 5.0 | | 4.8 | | 4.8 | |

| Components | | Example 5 First | Example 5 Second | Example 6 First | Example 6 Second | Comparative Example 1 First | Comparative Example 1 Second | Comparative Example 2 First | Comparative Example 2 Second |
|---|---|---|---|---|---|---|---|---|---|
| (Meth)acrylate polymerizable resin | | 30 | 30 | 30 | 30 | 30 | 30 | 30 | 30 |
| Mixing Ratio | Bis-GMA | | | | | 18 | 18 | | |
| | UDMA | 21 | 21 | 21 | 21 | 21 | 21 | 21 | 21 |
| | TEGDMA | 9 | | | | | 9 | | 9 |
| | HDMP | | 9 | | 9 | | | | |
| | NPGDMA | | | 9 | | 9 | | 9 | |
| Filler | | 70 | 70 | 70 | 70 | 70 | 70 | 70 | 70 |
| Mixing Ratio | b1 | 35 | 35 | 35 | 35 | 35 | 35 | 35 | 35 |
| | b2 | 56 | 57 | 60 | 50 | 60 | 60 | 60 | 59 |
| | b3 | 8 | 8 | 5 | 5 | 5 | 5 | 5 | 5 |
| | c1 | | | | 10 | | | | |
| | c2 | | 1 | | | | | | |
| | c3 | | | | | | | | 1 |
| Flexural Strength (Mpa) | | 124 | | 113 | | 95 | | 115 | |
| Setting Time | | 8 minutes and 30 seconds | | 8 minutes and 45 seconds | | 15 minutes | | 9 minutes and 15 seconds | |
| Light Curing Depth (mm) | | 4.6 | | 3.5 | | 5.2 | | 4.0 | |

What is claimed is:

1. A dental composite resin for core build-up comprising:
   a first component comprising a first (meth)acrylate polymerizable resin and an organic peroxide, and
   a second component comprising a second (meth)acrylate polymerizable resin and a reducing agent, wherein
   a photopolymerizaton initiator and one or more primary fillers having an average particle size of more than 0.2 μm are included in the first component and/or the second component,
   one or more secondary fillers having an average particle size of 0.2 μm or less are included in the first component and/or the second component,
   said secondary fillers being present in the first and/or second component in an amount of no more than 15% by weight of the respective component,
   said secondary fillers comprising an oxide powder of a Group II element in the periodic table having an average particle diameter of 0.01 to 0.2 μm,
   said oxide powder of a Group II element in the periodic table being present in the first and/or second component in an amount of 0.01 to 5% by weight of the respective component,
   the organic peroxide is selected from the group consisting of benzoyl peroxide, 2,4-dichlorobenzoyl peroxide, m-tolueneperoxide, t-butylperoxy benzoate, di-t-butylperoxyisophthalate, and 2,5-dimethyl-2,5 di(benzoylperoxy)hexane, and
   the reducing agent is at least one amine compound selected from the group consisting of N,N-dimethyl-p-toluidine, N,N-diethyl-p-toluidine, N,N-dimethylaniline, N,N-bis (2-hydroxyethyl)-p-toluidine, N,N-dimethylaminoethylmethacrylate, p-toluenediethanol amine, triethanol amine, p-dimethylamino methyl benzoate, p-dimethylamino ethyl benzoate, p-dimethylamino isoamyl benzoate, triethyl amine, and N-ethyldiethanol amine.

2. The dental composite resin according to claim 1, wherein the first (meth)acrylate polymerizable resin and the second (meth)acrylate polymerizable resin are individually selected from the group consisting of methyl(meth)acrylate, ethyl(meth)acrylate, isopropyl(meth)acrylate, 2-hydroxyethyl(meth)acrylate, 2-hydroxypropyl(meth)acrylate, 2-hydroxy-1,3-di(meth)acryloxypropane, n-butyl(meth)acrylate, isobutyl(meth)acrylate, butoxyethyl(meth)acrylate, hydroxypropyl(meth)acrylate, tetrahydrofurfuryl(meth)acrylate, glycidil(meth)acrylate, 2-methoxyethyl(meth)acrylate, 2-ethylhexyl(meth)acrylate, benzyl(meth)acrylate, ethyleneglycol di(meth)acrylate, diethyleneglycol di(meth)acrylate, triethyleneglycol di(meth)acrylate, triethyleneglycol tri(meth)acrylate, butyleneglycol di(meth)acrylate, neopentylglycol di(meth)acrylate, 1,3-butanediol di(meth)acrylate, 1,4-butanediol di(meth)acrylate, 1,6-hexanediol di(meth)acrylate, trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, polyoxytetraethylene-glycol di(meth)acrylate, 2,2-bis{(meth)acryloxyphenyl}propane, 2,2-bis[4-{2-hydroxy-3-(meth)acryloxypropoxy}phenyl]propane, 2,2-bis{4-(meth)acryloxydiethoxyphenyl}propane, 2,2-bis{4-(meth)acryloxypolyethoxyphenyl}propane, 2,2-bis[4(2-hydroxy-3-methacryloxypropoxy)phenyl]propane, and di-2-(meth)acryloxyethyl-2,2,4-trimethylhexamethylene dicarbamate.

3. The dental composite resin according to claim 1, wherein the first (meth)acrylate polymerizable resin is present in the first component in an amount of 10 to 60% by weight.

4. The dental composite resin according to claim 1, wherein the second (meth)acrylate polymerizable resin is present in the second component in an amount of 10 to 60% by weight.

5. The dental composite resin according to claim 1, wherein the organic peroxide is present in the first component is an amount of 0.01 to 5 parts by weight per 100 parts by weight of the first (meth)acrylate polymerizable resin.

6. The dental composite resin according to claim 1, wherein the reducing agent is present in the second component is an amount of 0.01 to 5 parts by weight per 100 parts by weight of the second (meth)acrylate polymerizable resin.

7. The dental composite resin according to claim 1, wherein the photopolymerization initiator is at least one compound selected from the group consisting of camphorquinone, benzyl, diacetyl, benzyl dimethyl ketal, benzyl diethyl ketal, benzyl di(2-methoxyethyl) ketal, 4,4'-dimethylbenzyl-dimethyl ketal, anthraquinone, 1-chloro-anthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethyl-thioxanthone, 2,4-diethylthioxanthone, 2,4-diisopropylthioxanthone, 2-chloro-7-trifluoro-methylthioxanthone, thioxanthone-10,10-dioxide, thioxanthone-10-oxide, benzo-inmethylether, benzoinethylether, isopropylether, benzoinisobutylether, benzophenone, bis(4-dimethylaminophenyl) ketone, 4,4'-bisdiethylaminobenzophenone, a derivative of an acylphosphine oxide, and a compound comprising an azide group.

8. The dental composite resin according to claim 1, wherein the photopolymerization initiator is present in the first and/or second component in an amount of 0.01 to 5 parts by weight per 100 parts by weight of the (meth)acrylate polymerizable resin in the respective component.

9. The dental composite resin according to claim 1, wherein the one or more primary fillers are selected from the group consisting of:
   an organic composite filler comprising an organic component and an inorganic component;
   a glass selected from the group consisting of a-quartz, silica, silicic acid anhydride, a barium glass, an alumina glass, a potassium glass, hydroxyapatite, a fluoroaluminosilicate glass, a barium borosilicate glass, and barium boro-alumina silicate glass; and
   a powder selected from the group consisting of synthetic zeolite, barium sulfate, titanium oxide, calcium phosphate, a feldspar, fumed silica, aluminum silicate, calcium silicate, magnesium carbonate, hydrous silicic acid, calcium silicate hydrate, and aluminum silicate hydrate.

10. The dental composite resin according to claim 1, wherein the one or more primary fillers are present in the first and/or second component in an amount of 40 to 90% by weight of the respective component.

11. The dental composite resin according to claim 1, wherein the oxide powder of a Group II element in the periodic table is an oxide powder of beryllium, magnesium, calcium, strontium or barium.

12. The dental composite resin according to claim 1, wherein the oxide powder of a Group II element in the periodic table is magnesium oxide.

* * * * *